(12) United States Patent
Ollivier et al.

(10) Patent No.: US 6,385,492 B1
(45) Date of Patent: May 7, 2002

(54) PROBE IMPLANTABLE IN THE CORONARY VENUS SYSTEM FOR STIMULATING THE LEFT HEART

(75) Inventors: Jean François Ollivier, Villiers-le-Bacle; Frédéric Bessoule, Savigny-sur-Orge; Philippe D'Hiver, Issy-les-Moulineaux; Philippe Ritter, Chatenay-Malabry, all of (FR)

(73) Assignee: ELA Medical, S.A., Montrouge (FR)

( * ) Notice: Subject to any disclaimer, the term of this patent is extended or adjusted under 35 U.S.C. 154(b) by 0 days.

(21) Appl. No.: 09/416,140

(22) Filed: Oct. 12, 1999

(30) Foreign Application Priority Data

Oct. 13, 1998 (FR) .............................................. 98 12772

(51) Int. Cl.$^7$ ................................................ A61N 1/05
(52) U.S. Cl. ....................................................... 607/122
(58) Field of Search .................................. 607/122, 125, 607/123

(56) References Cited

U.S. PATENT DOCUMENTS

| | | | |
|---|---|---|---|
| 4,627,439 A | * 12/1986 | Harris | |
| 5,322,509 A | 6/1994 | Rickard | ......................... 604/53 |
| 5,423,772 A | 6/1995 | Lurie et al. | .................. 604/282 |
| 5,476,498 A | 12/1995 | Ayers | ........................ 607/122 |
| 5,628,778 A | * 5/1997 | Kruse et al. | |
| 5,643,338 A | * 7/1997 | Bornzin et al. | |
| 5,683,445 A | 11/1997 | Swayer | ....................... 607/125 |

FOREIGN PATENT DOCUMENTS

EP  0 601 338  6/1994  ............ A61N/1/05

\* cited by examiner

*Primary Examiner*—Scott M. Getzow
(74) *Attorney, Agent, or Firm*—Orrick, Herrington & Sutcliffe LLP

(57) ABSTRACT

A probe for the stimulation of the left heart which is implantable in the coronary venus system. The probe is particularly useful for an active implantable medical device, in particular, pacemakers of the "multisite" type. The probe has a body, including a hollow sheath which elastically deformable and primarily deprived of any rigid element. The probe body has a distal extremity (34) which supports at least one stimulation electrode (54), and a stylet which is removable, and is able to be introduced inside the probe body and moveable in translation and rotation inside the probe body. The stylet is relatively rigid compared to the sheath and plastically deformable locally. The distal extremity (34) of the probe has, in the absence of stress, two curves, comprised in two distinct surfaces. The first surface (62) corresponds to an orientation curve laid down by a preform of the probe body. The second surface (64) corresponds to a support curve defined by a naturally bent form of the probe distal extremity (34). The probe distal extremity (34) is an auto-orienting extremity. The electrode is a sectoral electrode, having an active surface part (54) extending, in a radial plane, only on one sector of the probe body. This active surface is preferably turned in a direction that is appreciably perpendicular to the plane formed by the bent part (64) of the probe body distal extremity.

23 Claims, 5 Drawing Sheets

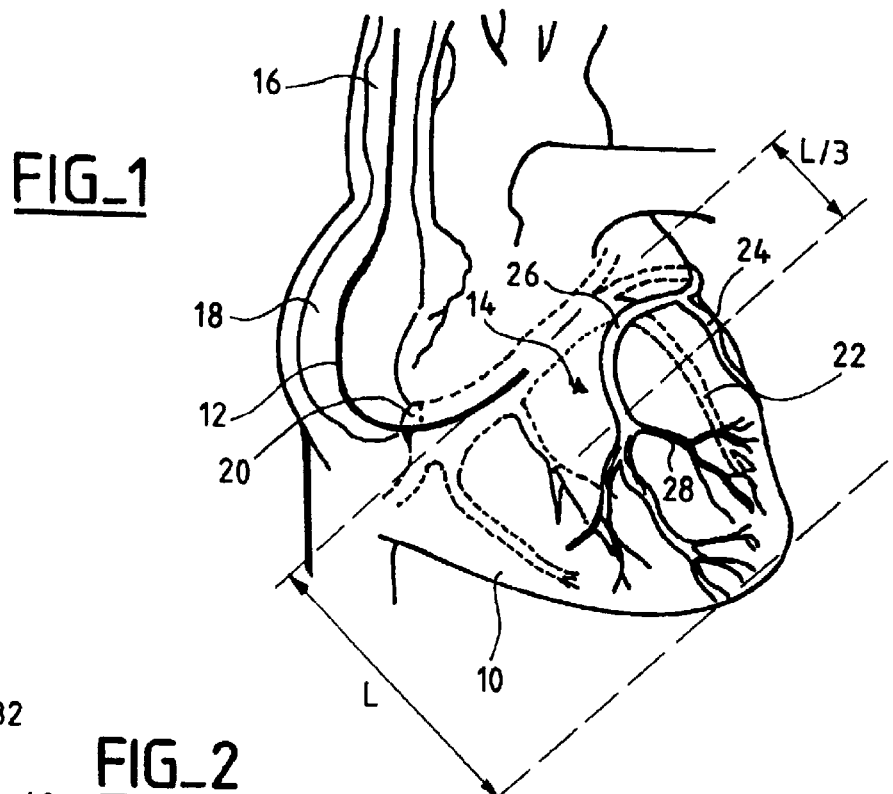
FIG_1
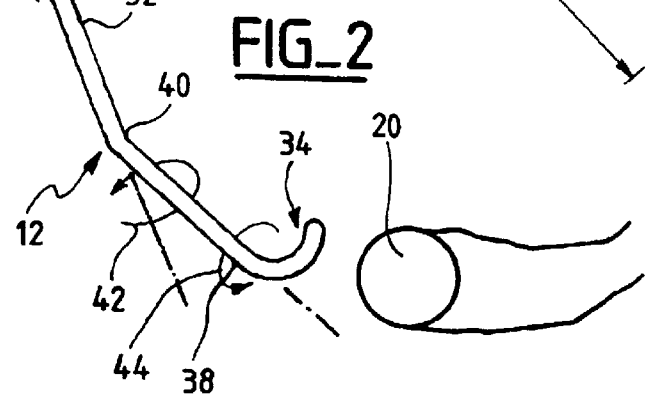
FIG_2
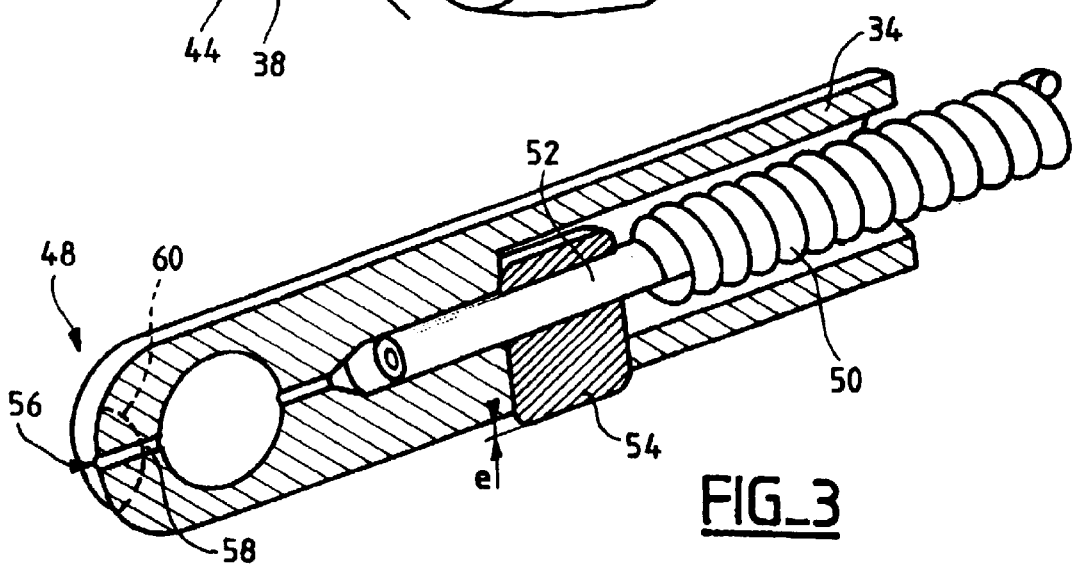
FIG_3

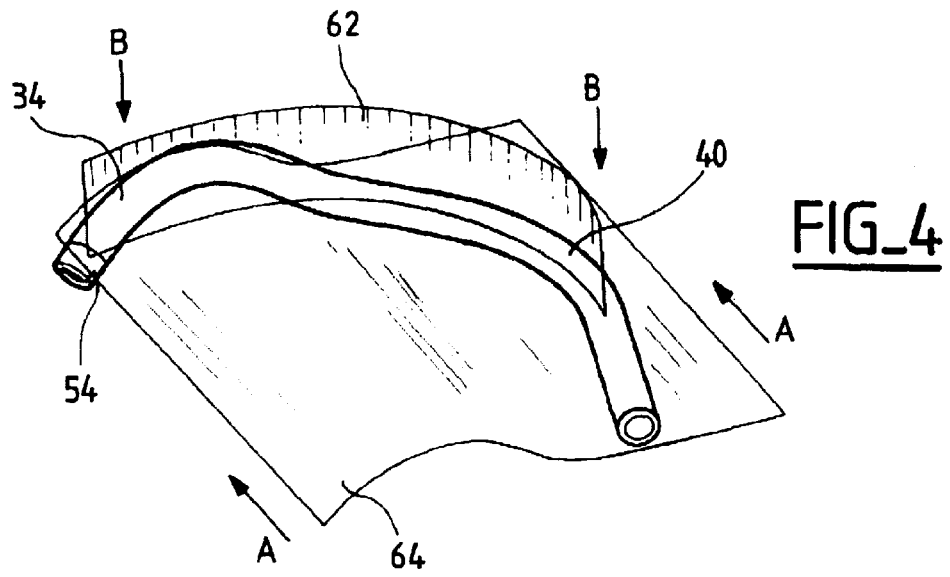
FIG_4
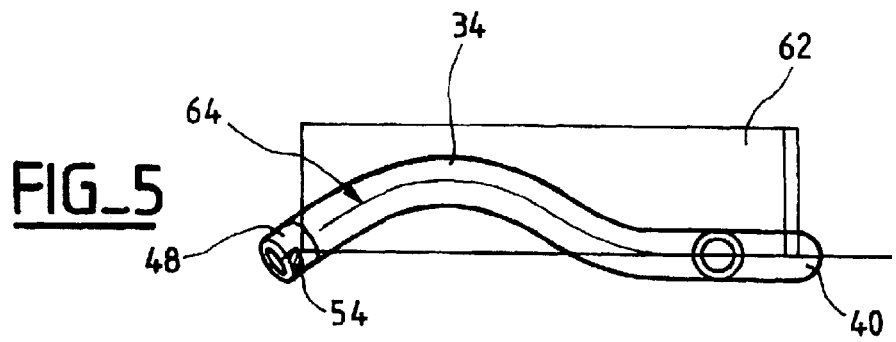
FIG_5
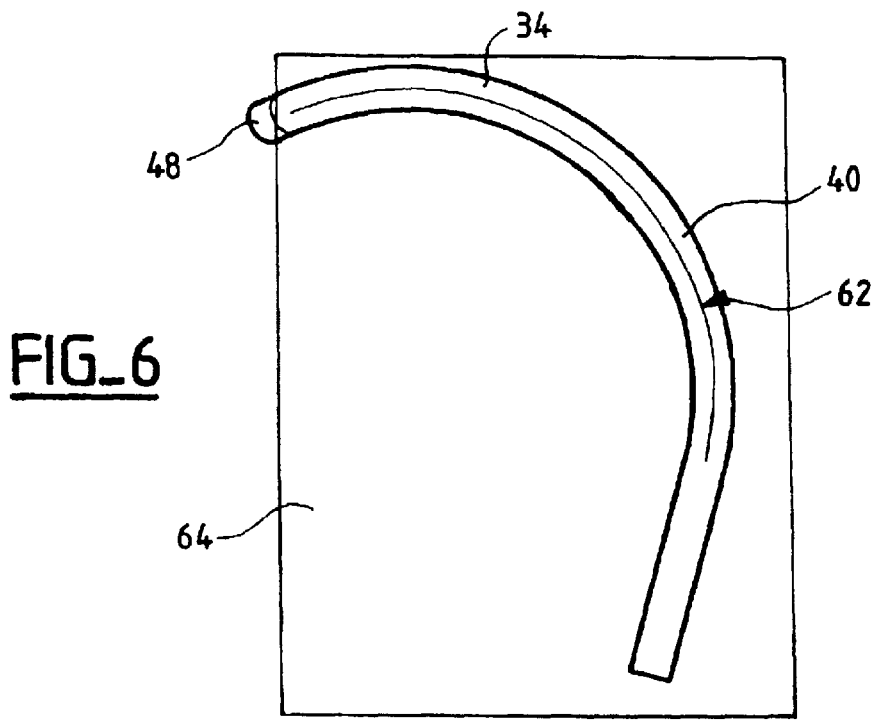
FIG_6

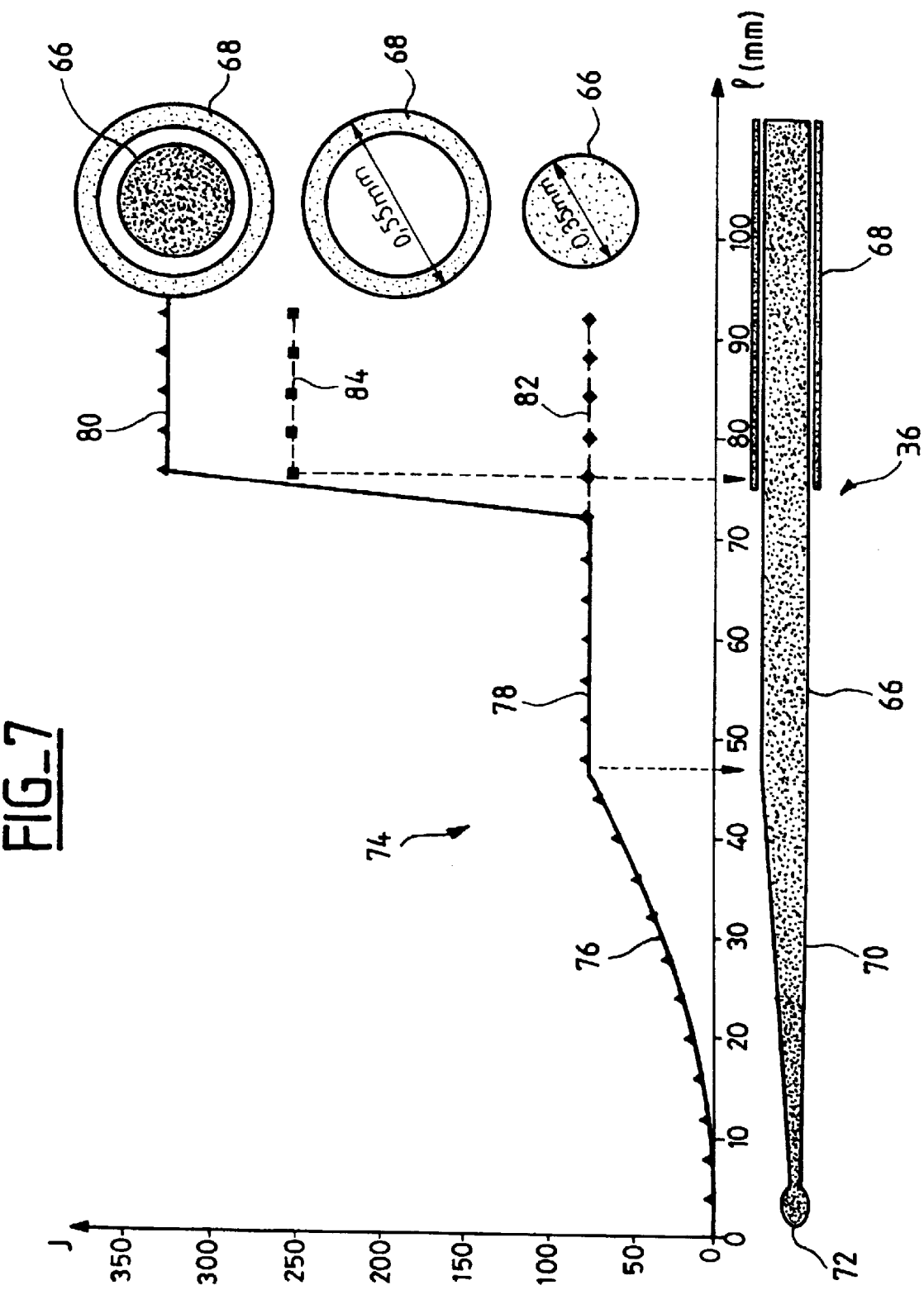
FIG_7

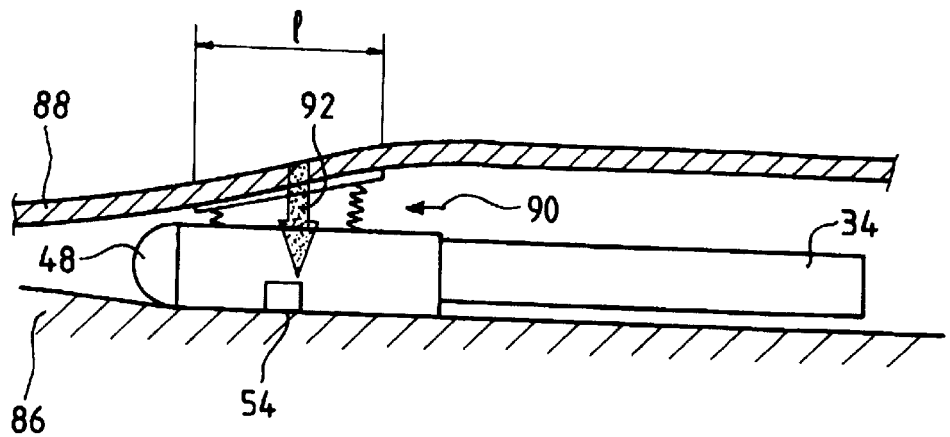
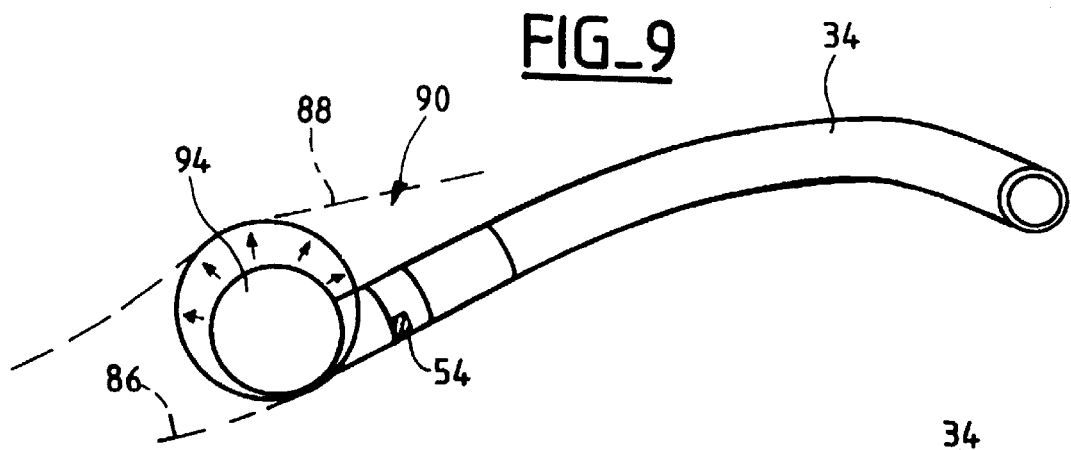
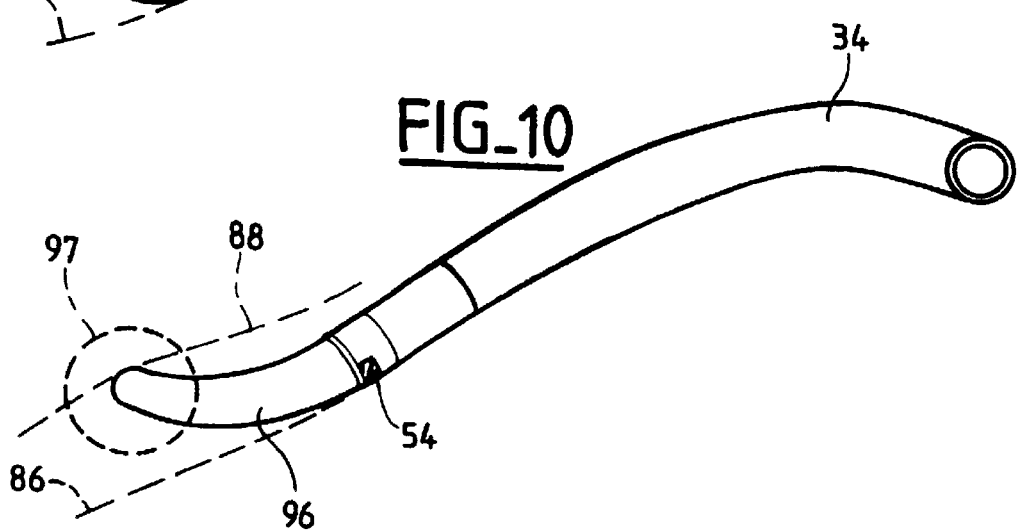

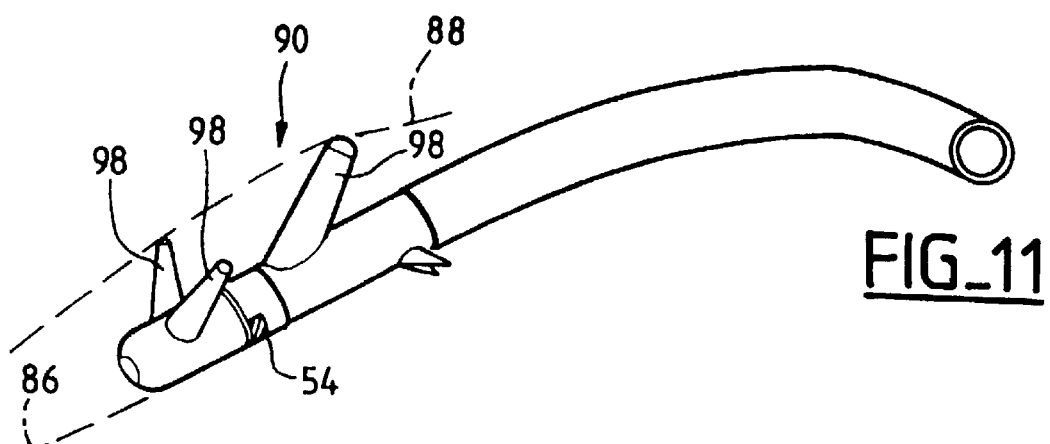
FIG._11
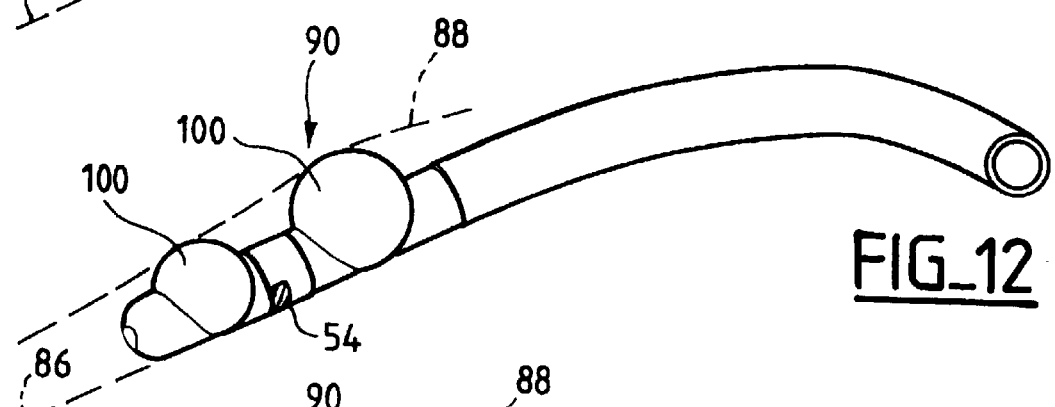
FIG._12
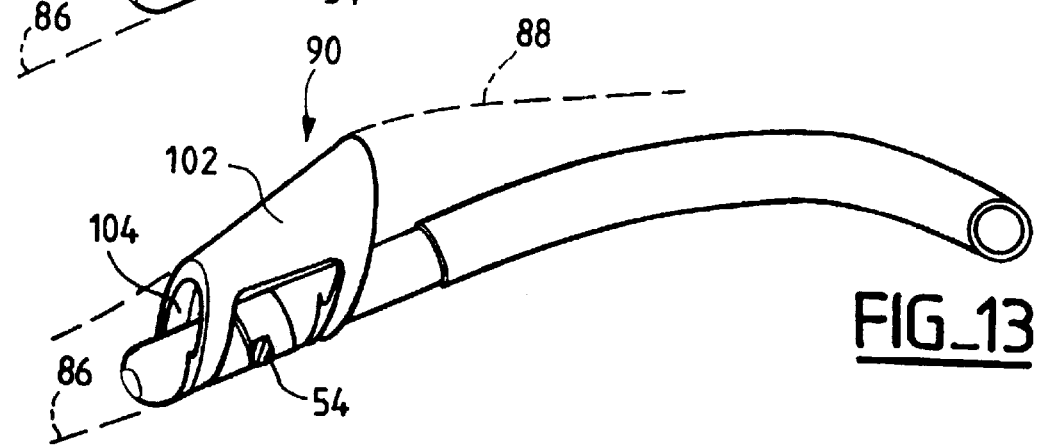
FIG._13
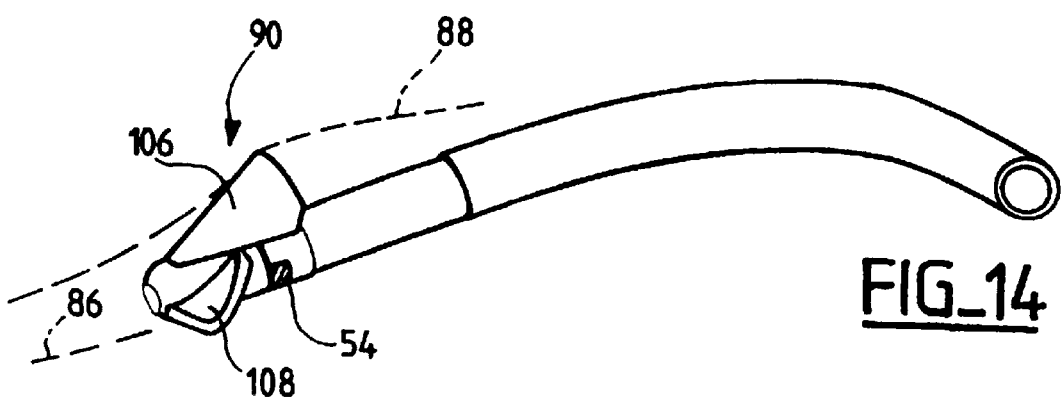
FIG._14

PROBE IMPLANTABLE IN THE CORONARY VENUS SYSTEM FOR STIMULATING THE LEFT HEART

FIELD OF THE INVENTION

The present invention relates to cardiac stimulation probes to be placed in the heart coronary system for the stimulation of the left ventricle or left atrium by an "active implantable medical device", as such devices are defined by the Jun. 20, 1990 directive 90/385/CEE of the Council of the European Communities, and more particularly by a device such as pacemaker, defibrillator and/or cardiovertor, notably a cardiac generator of "multisite" type.

BACKGROUND OF THE INVENTION

In contrast to the right ventricle, in which it is simple to implant endocardiac probes through the right peripheral venous system, the permanent installation of probes in a left heart cavity involves important operational risks. For example, there is a risk of bubbles passing towards the cerebral vascular system which is located downstream from the left ventricle. For this reason, one chooses in this case a probe to be introduced into the coronary system, with an electrode disposed against the left ventricle, with the probe access into the coronary sinus system being done via the right atrium.

The introduction of such a probe endocardially is a particularly delicate intervention. It is even more delicate when taking into account the fact that the position of stimulation sites is very important within the framework of "multisite" stimulation, in which the left ventricle and right ventricle stimulation sites are preferably as far part as possible, to optimize a resynchronisation of the cardiac cavities.

It is therefore important that this particular type of probe satisfy a certain number of precise criteria.

Firstly, the probe must be relatively rigid so that its distal end can be easily guided towards the entry of the sinus coronary at the time of implantation and introduced therein independent of any differences in morphology from one patient to the next (in certain pathologies, the atrium are sometimes very dilated), and to avoid pressing on the atrial wall.

Secondly, the probe must have a relative flexibility or suppleness, so that after having found the entry to the coronary sinus, and having introduced the distal extremity of the probe therein, the surgeon is able to move the probe easily in the coronary system. But, at the same time, the probe must have a certain rigidity so that the surgeon can push the probe, without too much difficulty, through obstructions, such as valves, and to transmit the surgeon's push to the distal end of the probe, ensuring that the probe does not form loops in the right atrium.

Thirdly, once the stimulation site is reached, the surgeon must be able to adjust easily the position of the probe (at present, the probe is very often simply wedged in an extremity of the vein) and, when the site is good, maintain the position of the probe regardless of the size of the vein.

Finally, it is desirable to be able to extract the probe at a later time without damaging the veins of the coronary system.

Ideally, all of these functions or characteristics must be present for a majority of surgeons to be able to use the system. In other words, the system must be sufficiently similar to the existing techniques and current practices to be used.

U.S. Pat. No. 5,683,445 refers to a probe of this type, with a unit made up of a probe body and a stylet. The probe body includes including an elastically deformable hollow sheath and is primarily deprived of any rigid elements, and a distal extremity that supports at least one stimulation electrode. The stylet is a removable stylet ready to be introduced inside the sheath of the probe body and moveable therein. The stylet is relatively rigid as compared to the sheath, and is locally plastically deformable. The distal extremity of the probe has, in the absence of stress, two curves formed of two distinct surfaces. The first surface corresponds to an orientation curve defined by a probe body preform. The second surface corresponds to a support curve defined by a naturally bent form of the probe distal extremity.

This probe construction, however, is not optimal in the field of electric stimulation. Indeed, the hemispherical end carrying the electrode ensures, because of its axial symmetry, an identical placement of the active surface against the myocardium, regardless of the orientation of the probe extremity. But, because of the hemispherical end, this probe structure presents several serious disadvantages, in particular, a risk of parasitic stimulation of the nerves by the electric stimulus, and a low current density, and therefore a relatively lower physiological effectiveness and larger consumption of energy.

OBJECT AND SUMMARY OF THE INVENTION

It is, therefore, an object of the present invention to cure the aforementioned disadvantages, by proposing an improvement of probe of the type generally taught by U.S. Pat. No. 5,683,445, which is optimised for electrical stimulation.

To this end, the present invention is directed to providing a probe having a distal extremity which has an elbow and is self-directional (auto-orienting) during installation. The probe has an electrode which is a sectoral electrode, having an active surface portion on the side of the probe extending, in a radial plane, only on one sector of the probe body. The sectoral electrode active surface is preferentially turned in a direction that is appreciably perpendicular to a plane formed by the elbow of the probe body distal extremity and protrudes from the surface of the probe body in a radial plane similar to the curve of the probe body distal extremity.

In accordance with a preferred embodiment, the removable stylet has a distal extremity which is provided with a ball at its distal end. The stylet preferably comprises a core having a distal portion and a proximal portion, and a reinforcement tube over the core such that the core is sheathed over its proximal portion by the reinforcement tube, which increases the rigidity of the stylet proximal portion. The stylet core emerges from the reinforcement tube at the distal part, and the distal part thus has a relatively greater flexibility.

In one embodiment, the probe body distal extremity comprises an axial passageway which is maintained sealed closed in the absence of an external or interior stress on the axial passageway, and which has an opened condition which allows a small stylet, more particularly an angioplasty stylet, to penetrate and pass through the axial passageway and so to extend beyond the probe body distal extremity. This occurs when the angioplasty stylet is substituted for the stylet initially introduced into the probe body, as discussed below.

In another embodiment, the probe body distal extremity comprises an elastic system that is resiliently urged against the inner vein wall. The elastic system is positioned on the distal extremity diametrically opposite to the active surface of the electrode, and thus aids in maintaining the electrode active surface in conducting contact with the myocardium wall. Preferably, the elastic system is a counter-elbow, also extending in a plane approximately perpendicular to the plane formed by the elbow of the probe distal extremity. Alternately or in addition, the elastic system can be one or more elastically deformable bodies projecting from the probe surface, which bodies are interposed between the inside of the external wall of the vein and surface of the myocardium.

BRIEF DESCRIPTION OF THE DRAWINGS

Other characteristics, features and advantages of the present invention will appear to a person of ordinary skill in the art in view of the following detailed description, made with reference to the annexed drawings, in which like reference characters refer to like elements, and in which:

FIG. 1 illustrates the heart and its venous coronary system in which a probe in accordance with a preferred embodiment of the present invention is being introduced;

FIG. 2 schematically illustrates the configuration of the probe of FIG. 1, with its degrees of freedom, in the vicinity of the entry to the coronary sinus;

FIG. 3 is a longitudinal section of the distal extremity of the probe of FIG. 1 in accordance with a preferred embodiment of the invention;

FIG. 4 is an elevated perspective view of the shape of distal extremity of the probe of FIG. 1 in space (unstressed);

FIG. 5 is an end view, according to line A—A, of the probe of FIG. 4;

FIG. 6 is a top view, according to line B—B, of the probe of FIG. 4;

FIG. 7 shows a length of the stylet including the distal end portion in relation to the corresponding characteristic giving the moment of inertia along its length;

FIG. 8 is a diagrammatic representation illustrating the function of the elastic support against the vein; and FIGS. 9 to 14 respectively illustrate six embodiments of the elastic system for supporting the probe in position.

DETAILED DESCRIPTION OF THE INVENTION

Referring to FIG. 1, reference 10 indicates in a general way the myocardium, into which one has started to introduce a probe 12 of the present invention intended for use in the stimulation of the left ventricle. This probe 12 is introduced endocardially into the venous coronary system, indicated in a general way by the reference 14, via the high vena cava 16, the right atrium 18 and entry 20 of the venous coronary sinus. The venous coronary system then develops several branches, including the cardiac posterior-lateral veins 22, lateral veins 24, the large cardiac vein 26, and the antero-lateral vein 28.

It is the fact that when advancing the distal extremity of the probe, the extremity, which is provided with the stimulation electrode, comes to rest against the venous wall, on the side of the heart, positioned at the left ventricle. In practice, one seeks to reach a stimulation site located at a distance of approximately L/3 of the principal vein, L being the distance between the base of the principal vein and the tip of the ventricle. If this optimal location is not respected, it is necessary to go further along the vein in order to position the probe extremity at a suitable stimulation site. If the site is not optimal, then it is typically necessary to increase the stimulation energy to obtain the required effect.

In order that the probe can be easily guided towards opening 20 of the venus coronary system 14, and then inside the various veins of the coronary system, the probe 12 in accordance with the invention has the general, known structure such as is illustrated in FIG. 2.

Essentially, probe 12 comprises a probe body 32 made of a flexible material which is elastically deformable (typically a silicone), which has at its distal extremity a bent form (such as a curvature or a bent part or an elbow) 34. At rest, i.e., in the absence of interior and external stress on the probe body, the elbow 34 is, for example, an elbow of approximately 90°, having a radius of from 10 to 20 mm. The probe body is hollow, so as to allow the introduction of a stylet 36 made of a relatively rigid material (typically a type MP35N stainless steel wire), which one can insert into the probe body to a greater or lesser distance so as to vary the curvature of the elbow 34. Thus, in the illustrated configuration where the stylet 36 is inserted to position the distal extremity 38 right before (proximal to the elbow 34), the original, natural bent form is preserved. On the other hand, if one inserts stylet 36 more deeply in the probe body 32, the rigidity of the stylet will straighten elbow 34 thus reduce its curvature.

In addition, the stylet 36 can be deformed by the surgeon, for example, bent in the form of a local deformation 40 to allow a better general orientation of the elbow 34 as it approaches, and to facilitate its access into, the entry 20 of the venous coronary system.

One thus obtains a system with three degrees of freedom, namely: a first degree of freedom in rotation (arrow 42; FIG. 2) around the more proximal part of the probe body, so as to allow a global approach to entry 20 of the sinus by rotation of the stylet 36 and probe body 32; a second degree of freedom in rotation (arrow 44; FIG. 2) by rotation of the probe body 32 around stylet 36, stylet 36 being maintained fixed, to allow a finer approach; and a third degree of freedom in translation (arrow 46; FIG. 2) by the relative penetration of stylet 36 inside probe body 32 (depth of penetration), making it possible to vary the final curve or shape of elbow 34.

The simultaneity of these various movements, added to the overall translation of probe 12, makes it possible to enter the venous coronary system relatively easily.

FIG. 3 illustrates more precisely a preferred embodiment of the structure of distal extremity 48 of the probe body. Imbedded inside the flexible material of the probe body 32 is a spiral metal conductor 50. Conductor 50 is in contact at its extremity with a hollow tube 52, which is in contact with the electrode 54. According to the invention, electrode 54 is an electrode of the sectoral type for the reasons which will be described further with reference to FIGS. 8 to 14. At its distal end, the probe 12 optionally and advantageously comprises an axial passageway 56, normally sealed closed by a joint 58, but able to be opened and penetrated, in a close fitting way, by a smaller diameter stylet such as an angioplasty stylet (as will be explained below). To reinforce the sealing caused by joint 58, one can advantageously envisage a frontal cavity 60 (shown in phantom lines) which retains blood and subsequently forms a clot in the cavity at the entrance to passageway 56 once the probe is definitively installed.

Referring now to FIGS. 4 to 6, the spatial position of the probe in the phase of approaching the opening of the venous coronary system, is illustrated. The trajectory of the tube in fact is defined by the intersection of two surfaces 62, 64. Surface 62 corresponds to an orientation curve, and it is defined by the preform or natural shape of the silicone tube, and surface 64 corresponds to a support curve resulting from the naturally bent form of the distal extremity part 34 of the probe.

Once the probe 12 distal end has reached the entry of the sinus by the above mentioned technique, it nevertheless remains to overcome many obstacles.

Indeed, at the time of its progression in the pathways of the venous coronary system, the probe 12 encounters several difficulties: frictions, jamming, blood vessel branching, sequences of the curves, reduction in diameter of the vein, valvule passages, etc. which require an increasingly strong push on the probe to advance it through the coronary system. If the unit formed by the probe body and the stylet inserted in the probe is too flexible, the unit buckles under the pushing force in the right atrium, with a risk of disengaging the probe from contact with of the sinus. To avoid this risk, a technique is employed whereby the probe stylet unit is withdrawn a few centimeters, and the probe body is moved relative to the stylet, which is maintained fixed in position. This provides the unit with additional support based on the greater rigidity of the stylet, and the probe/stylet unit is thus made more rigid and better able to transmit the pushing force to the probe extremity.

In addition, to facilitate the introduction of the stylet into a probe which already has been introduced into the sinus, the stylet is advantageously provided with a shaped distal extremity, such as is illustrated in cross section in FIG. 7. Also illustrated on FIG. 7 is a representation of a preferred characteristic of the moment of inertia J along the stylet length 1, corresponding to the illustrated shape of stylet. FIG. 7 is shown drawn to a length scale in units of mm.

Stylet 36 thus comprises a full cylindrical part 66, typically with a diameter 0.35 mm, sheathed over the major part of its length by a reinforcement tube 68, the overall diameter of the whole stylet being typically approximately 0.50 mm at its thickest point inside the probe.

The distal side of the stylet extremity is bare, that is it is not encased by the reinforcement tube 68. The bare portion in this embodiment extends over a total length of approximately 70 mm. The bare extremity ends in a tapered part 70, having a length of approximately 40 mm, which is provided at its distal extremity with a ball 72. Ball 72 is provided to limit friction on the spirals of the internal conductor 50 (FIG. 3) and to thus avoid dislodging the probe and perforating the probe.

This particular stylet structure has a variable rigidity, as can be seen on the characteristic 74 giving the moment of inertia J, relating to the point considered along the stylet length 1.

This characteristic 74 comprises an initial very flexible portion 76, corresponding to the tapered part 70, making it possible to introduce easily the stylet into the probe body, particularly when the probe body is already introduced into the sinus.

The stylet portion 78 is an area still having a relatively low moment of inertia, but it is slightly less flexible than the distal portion 76, also to allow the easy introduction into the sinus.

Next, in the proximal direction, the moment of inertia presents an abrupt increase in the area 80, which corresponds to the addition of the moment of inertia 82 of the cylindrical core 66 and of the moment of inertia 84 of the reinforcement tube 68. This greater rigidity makes it possible to transmit, without difficulty, the increasingly higher insertion force or "push," as necessary to overcome the various obstacles met by the probe in passing into the venous system.

Once the probe is sufficiently introduced into the sinus, it can be advantageous to replace the aforementioned stylet 36 with a smaller diameter stylet, preferably an angioplasty stylet, i.e., a very fine stylet comprising a metal core sheathed by a spring and whose flexible extremity can be introduced directly into the blood vessels without risk of perforation.

Such an angioplasty stylet can be introduced into the central cavity of the probe body through the reinforcement tube 68 (thus avoiding any dislodgement of the probe), penetrate joint 58 (FIG. 3) and progress then, alone, into the coronary system. Thus, the angioplasty stylet can be used by the surgeon to select more easily a collateral vein. Once the vein is selected, one will then be able to continue inserting the probe body by passing it along the angioplasty stylet, whose role will be that of a simple "guide" having a small diameter along which the probe passes.

In addition, because of the curve of the elbow 34, while turning the probe, it is possible to present its extremity to the entry of the target vein, and thus to facilitate its access.

In connection with the insertion of a bipolar probe, because it is desirable to have a highly flexible probe in order to avoid any inopportune wedging, it would be advantageous to have the proximal electrode formed of a simple spring, e.g., made of platinum-iridium, in order to avoid introducing the rigidity which exists with a conventional external ring electrode.

In accordance with characteristic of the present invention, as is illustrated in FIGS. 3 and 8, electrode 54 is a sectoral electrode, i.e., the active electrode area extends in a radial plane only on one sector of the probe body surface, and not on the circumference (FIG. 8 is a representation in a plane perpendicular to the plane P defined by the curve of the elbow 34). This configuration allows, in the case of the stimulation of the left ventricle via a vein of the coronary system, that the electrode active surface is turned towards the interior of the myocardium. Advantageously, this sectoral electrode structure avoids the parasitic stimulation of nerves which otherwise could be excited by the electric stimulus.

In addition, by reducing the electrode active surface area (typically to an area of about 2 $mm^2$), one obtains the advantages of a probe having a "high current density". This provides increased physiological effectiveness of the stimulation and reduced energy consumption.

If the sectoral electrode active surface 54 is positioned perpendicular to the plane formed by elbow 34 (see for example FIGS. 9 to 14), this configuration allows an automatic positioning of the electrode active surface towards the interior of the heart. Indeed, this position is the lowest stress position of the probe body elbow and the elbow is thus "auto-orienting" as a consequence of its geometry.

Moreover, because the electrode is directed towards the myocardium, it also is desirable to exert a light pressure on the electrode in order to establish a reliable touching and conductive contact independent of the cardiac movements, and eliminate any risk from floating in the vein.

For this purpose, as is schematically illustrated in FIG. 8, to improve the stability of probe extremity 48 in the desired position, between myocardium 86 and the wall 88 of the vein, an elastic system 90 is provided, exerting a pressure on wall 88 so as to generate by reaction a force, schematized by the arrow 92, which will press electrode 54 against, and perhaps somewhat into, the surface of myocardium 86. Moreover, the elastic system, which preferably extends over a relatively long area 1, makes it possible to wedge mechanically in place the probe head and minimize any withdrawal or inopportune movement of the probe.

The elastic system 90 is preferably positioned diametrically opposite to the active surface of electrode 54, and can be implemented in various ways, including but not limited to, the particular structures illustrated as examples in FIGS. 9 to 14.

Further, and as one can see in the illustration on FIG. 3, the electrode active area 54 projects slightly by a distance "e" above the probe surface in order to maintain good contact with the corresponding area of the myocardium.

In the embodiment illustrated in FIG. 9, the elastic system 90 comprises a ball 94 located downstream (in the distal direction) of electrode 54. This ball 94 allows in particular an effective wedging in all directions, and an easy withdrawal of the probe. Advantageously, the ball 94 can be formed of a material that is charged with a steroid having a controlled release over time, as such techniques are known to persons skilled in the art. The ball may be made of silicone charged with the steroid and advantageously may have the property to increase its volume due to the absorption of fluids.

The ball 94 also can be made inflatable and deflatable through the use of an interior passageway of the probe body. In this case, a depressurization compresses or deflates the ball 94 for insertion, then one fills the ball 94 with air (or a biocompatible gas or fluid) so that it obtains its natural or original spherical form. In an alternative, ball 94 can be also inflated in situ, in particular, with an injection of a radiopaque fluid which has an advantage as compared to the tubes of the so-called "peeling system" type.

In the embodiment illustrated in FIG. 10, the elastic system 90 includes a counter-elbow 96, positioned downstream from (distally of) electrode 54. This embodiment is particularly preferred because it presents many advantages. First, one obtains a smooth monolithic probe with a small size, deprived of projecting bodies such as barbs, spheres or other systems of fixing the probe in position. Second, this probe offers a broad operating range, with a large clearance of the support curve, typically about three times the diameter of the vein, guaranteeing a good electrode/endocardial contact which is in the dimension of the vein. The counter-elbow also assists in guiding the probe within the venus system. Because the retention is being ensured by elbow 34 and counter-elbow 96, it is not essential to introduce the probe to the end of the vein, which allows an optimization of the choice of the stimulation site and a better overall depolarization of the two ventricles (for example, by maximizing the distance between the stimulation sites in the left ventricle and the right ventricle). Further, the device is relatively easy to manufacture, the technique of manufacturing the tube being comparable with that of the so-called "J" atrial probe. In addition, the probe is easy to extract if necessary, because of the absence of any barbs to be rolled up or a ball to be compressed or deflated.

In an alternative of this embodiment, it is possible to also provide a sphere 97 (shown in phantom lines) at the extremity of counter-elbow 96, to locally distribute the pressure exerted on the wall of the vein by the distal end of counter-elbow 96 over a greater surface.

In the embodiment illustrated in FIG. 11, elastic system 90 is a series of barbs 98 which are located upstream and/or downstream from electrode 54. It is necessary to note that, unlike the barbs of the traditional endocardiac probes, the principal function of these barbs 98 is to provide an elastic support for holding the probe head between wall 88 of the vein and myocardium 86 and not for mechanical retention against withdrawal, although the barbs 98 could perform a subsidiary function of resisting extraction.

In the embodiment illustrated in FIG. 12, elastic system 90 includes a series of two or more spheres 100 located upstream and downstream from electrode 54. The various remarks made above in connection with the single ball embodiment illustrated in FIG. 9 also are applicable to this embodiment having two or more spheres.

In the embodiment illustrated in FIG. 13, elastic system 90 comprises a roof 102 located remotely from and resiliantly connected to the probe by mounts 104. Mounts 104 are flexible structures, e.g., beams or tubes, and thus allow for a depression of the roof 102 against the probe body during the introduction of the probe.

In the embodiment illustrated in FIG. 14, elastic system 90 comprises a skirt section 106, which acts in a manner comparable with that of barbs 98 of the embodiment illustrated in FIG. 11. The skirt 106 is preferably combined with ailerons 108 which are attached to the probe for the guidance of the probe at the time of its descent in the venous coronary system.

Although only one electrode active surface 54 is illustrated, it should be understood that more than one electrode surface may be supported by the probe, and each electrode may use the same or a different elastic system 90, depending on the particular application.

One skilled in the art will appreciate that the present invention can be practiced by other than the described embodiments, which are presented for the purposes of illustration and not of limitation.

We claim:

1. A system for the stimulation of the myocardium in the coronary venous system, for an active implantable medical device, comprising:

a probe body, including a hollow sheath, the hollow sheath being elastically deformable, the probe body having a distal extremity having thereon at least one stimulation electrode and having a naturally bent form; and a removable stylet, adapted to be introduced and movable inside the hollow sheath of the probe body, said stylet being more rigid than the hollow sheath and plastically deformable at any point along its length;

wherein the probe distal extremity in the absence of stress comprises a first curve comprised in a first surface and a second curve comprised in a second surface distinct from the first surface, the first surface corresponding to a support curve in a first plane defined by the naturally bent form of the probe distal extremity, characterized in that the probe distal extremity is an auto-orienting extremity, and wherein the at least one stimulation electrode further comprises a sectoral electrode having an active surface extending in a radial plane on only one sector of the probe body, said radial plane being perpendicular to said first plane, said first curve and said second curve cooperating to position said sectoral electrode against the myocardium when said probe body distal end is in said coronary venous system.

2. The system of claim 1, wherein the active sectoral electrode surface projects a distance above the probe body distal extremity.

3. The system of claim 1, wherein the stylet has a distal extremity and said distal extremity comprises a tapered section having a distal end and a ball at said tapered section distal end.

4. The system of claim 1, wherein the stylet comprises a core and a reinforcement tube (68), the core having a distal part and a proximal part and said reinforcement tube disposed over at least a portion of said core proximal part to form a sheathed core section, wherein the sheathed core section has a rigidity greater than the core distal part, and wherein the core distal part has a flexibility that is greater than the sheathed core section.

5. A system according to claim 1, in which the probe body distal extremity comprises a passageway for axial penetration, said passageway having a sealed condition in the absence of an external or interior stress, and an opened condition allowing the passage therethrough and the progression beyond the probe body distal extremity of an angioplasty stylet.

6. The system of claim 1, in which the probe body distal extremity comprises an elastic system to provide support against a vein, said elastic system being positioned opposite to the electrode active surface.

7. The system of claim 6 wherein the natural bent form of said distal extremity further comprises a curvature in a first plane and the elastic system further comprises a counter-elbow distal of said curvature and extending in a second plane perpendicular to the first plane.

8. The system of claim 7 wherein the counter-elbow is positioned distally of said curvature.

9. The system of claim 7 wherein the curvature further comprises an elbow.

10. The system of claim 6, wherein the elastic system further comprises at least one elastically deformable body projecting from said probe body distal extremity and adapted to be interposed between an interior surface of an external wall of a vein and a myocardium surface.

11. The system of claim 1 wherein the bent form of said probe body distal extremity further comprises a first portion and a second portion connected by a curvature in a first plane.

12. The system of claim 11 wherein the curvature further comprises a radius of between 10 and 20 mm said first and second portions are oriented at 90°.

13. A system for the stimulation in the coronary venous system, for an active implantable medical device, comprising:
  a probe body, including a hollow sheath, the hollow sheath being elastically deformable, the probe body having a distal extremity having thereon at least one stimulation electrode and having a naturally bent form; and
  a removable stylet, adapted to be introduced and movable inside the hollow sheath of the probe body, said stylet being more rigid than the hollow sheath and plastically deformable at any point along its length, wherein the stylet has a distal extremity and said distal extremity comprises a tapered section having a distal end and a ball at said tapered section distal end;
  wherein the probe distal extremity in the absence of stress comprises two curves comprised in a first surface and a second surface distinct from the first surface, the first surface corresponding to a support curve defined by the naturally bent form of the probe distal extremity, characterised in that the probe distal extremity is an auto-orienting extremity, and wherein the at least one stimulation electrode firther comprises a sectoral electrode having an active surface extending in a radial plane on only one sector of the probe body.

14. The system of the claim 13, wherein the probe body distal extremity further comprises an elbow, the elbow defining a plane, wherein the sectoral electrode active surface is oriented in a direction appreciably perpendicular to said plane.

15. The system of claim 13, wherein the active sectoral electrode surface projects a distance above the probe body distal extremity.

16. A system for the stimulation in the coronary venous system, for an active implantable medical device, comprising:
  a probe body, including a hollow sheath, the hollow sheath being elastically deformable, the probe body having a distal extremity having thereon at least one stimulation electrode and having a naturally bent form; and
  a removable stylet, adapted to be introduced and movable inside the hollow sheath of the probe body, said stylet being more rigid than the hollow sheath and plastically deformable at any point along its length;
  wherein the probe distal extremity in the absence of stress comprises two curves comprised in a first surface and a second surface distinct from the first surface, the first surface corresponding to a support curve defined by the naturally bent form of the probe distal extremity, characterised in that the probe distal extremity is an auto-orienting extremity, and wherein the at least one stimulation electrode further comprises a sectoral electrode having an active surface extending in a radial plane on only one sector of the probe body; and
  wherein the stylet comprises a core and a reinforcement tube, the core having a distal part and a proximal part and said reinforcement tube disposed over at least a portion of said core proximal part to form a sheathed core section, wherein the sheathed core section has a rigidity greater than the core distal part, and wherein the core distal part has a flexibility that is greater than the sheathed core section.

17. A system for the stimulation in the coronary venous system, for an active implantable medical device, comprising:
  a probe body, including a hollow sheath, the hollow sheath being elastically deformable, the probe body having a distal extremity having thereon at least one stimulation electrode and having a naturally bent form; and
  a removable stylet, adapted to be introduced and movable inside the hollow sheath of the probe body, said stylet being more rigid than the hollow sheath and plastically deformable at any point along its length;
  wherein the probe distal extremity in the absence of stress comprises two curves comprised in a first surface and a second surface distinct from the first surface, the first surface corresponding to a support curve defined by the naturally bent form of the probe distal extremity, characterised in that the probe distal extremity is an auto-orienting extremity, and wherein the at least one stimulation electrode further comprises a sectoral electrode having an active surface extending in a radial plane on only one sector of the probe body, wherein the probe body distal extremity comprises a passageway for axial penetration, said passageway having a sealed condition in the absence of an external or interior stress, and an opened condition allowing the passage therethrough and the progression beyond the probe body distal extremity of an angioplasty stylet.

18. A system for the stimulation in the coronary venous system, for an active implantable medical device, comprising:

a probe body, including a hollow sheath, the hollow sheath being elastically deformable, the probe body having a distal extremity having thereon at least one stimulation electrode and having a naturally bent form; and a removable stylet, adapted to be introduced and movable inside the hollow sheath of the probe body, said stylet being more rigid than the hollow sheath and plastically deformable at any point along its length;

wherein the probe distal extremity in the absence of stress comprises two curves comprised in a first surface and a second surface distinct from the first surface, the first surface corresponding to a support curve defined by the naturally bent form of the probe distal extremity, characterised in that the probe distal extremity is an auto-orienting extremity, and wherein the at least one stimulation electrode further comprises a sectoral electrode having an active surface extending in a radial plane on only one sector of the probe body, wherein the probe body distal extremity comprises an elastic system to provide support against a vein, said elastic system being positioned opposite to the electrode active surface.

19. The system of claim 18 wherein the natural bent form of said distal extremity further comprises a curvature in a first plane and the elastic system further comprises a counter-elbow distal of said curvature and extending in a second plane perpendicular to the first plane.

20. The system of claim 20 wherein the counter-elbow is positioned distally of said curvature.

21. The system of claim 19 wherein the curvature further comprises an elbow.

22. The system of claim 18, wherein the elastic system further comprises at least one elastically deformable body projecting from said probe body distal extremity and adapted to be interposed between an interior surface of an external wall of a vein and a myocardium surface.

23. The system of claim 18 wherein the bent form of said probe body distal extremity further comprises a first portion and a second portion connected by a curvature in a first plane.

* * * * *

UNITED STATES PATENT AND TRADEMARK OFFICE
CERTIFICATE OF CORRECTION

PATENT NO.    : 6,385,492 B1
DATED         : May 7, 2002
INVENTOR(S)   : Jean Fracais Olivier et al.

It is certified that error appears in the above-identified patent and that said Letters Patent is hereby corrected as shown below:

Column 1,
Line 33, delete "part" and insert -- apart -- therefor;

Column 2,
Line 3, delete "including";

Column 4,
Line 23, delete "34 thus" and insert -- 34 and thus -- therefor; and

Column 5,
Line 16, delete "with of the" and insert -- with the -- therefor;

Signed and Sealed this

Twenty-sixth Day of July, 2005

JON W. DUDAS
*Director of the United States Patent and Trademark Office*